US012569112B2

(12) United States Patent
Yamamura

(10) Patent No.: US 12,569,112 B2
(45) Date of Patent: Mar. 10, 2026

(54) IMAGING DEVICE, ENDOSCOPE SYSTEM, CONTROL UNIT, AND IMAGING METHOD

(71) Applicant: OLYMPUS MEDICAL SYSTEMS CORP., Hachioji (JP)

(72) Inventor: Daiki Yamamura, Hachioji (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 257 days.

(21) Appl. No.: 18/411,307

(22) Filed: Jan. 12, 2024

(65) Prior Publication Data

US 2024/0148233 A1 May 9, 2024

Related U.S. Application Data

(63) Continuation of application No. PCT/JP2021/027162, filed on Jul. 20, 2021.

(51) Int. Cl.
*A61B 1/00* (2006.01)
*A61B 1/045* (2006.01)
*A61B 1/05* (2006.01)

(52) U.S. Cl.
CPC ...... *A61B 1/00006* (2013.01); *A61B 1/00025* (2013.01); *A61B 1/045* (2013.01); *A61B 1/05* (2013.01)

(58) Field of Classification Search
CPC .............................. A61B 1/05; A61B 1/00114
See application file for complete search history.

(56) References Cited

U.S. PATENT DOCUMENTS

| | | | | |
|---|---|---|---|---|
| 2019/0165786 A1* | 5/2019 | Shimada | ........... | H04L 25/03019 |
| 2019/0268559 A1* | 8/2019 | Kondo | ................. | H04N 25/709 |
| 2020/0036923 A1* | 1/2020 | Goto | ..................... | H04N 25/709 |
| 2021/0058578 A1* | 2/2021 | Kudoh | .................... | H10F 39/18 |
| 2021/0274117 A1* | 9/2021 | Chiba | .................... | H04N 25/78 |
| 2021/0337119 A1* | 10/2021 | Nishino | ............... | H04N 23/667 |

FOREIGN PATENT DOCUMENTS

| | | |
|---|---|---|
| JP | 56-177 U | 1/1981 |
| JP | 2012-175484 A | 9/2012 |
| JP | 2016-214571 A | 12/2016 |

OTHER PUBLICATIONS

International Search Report dated Oct. 19, 2021, issued in counterpart International Application No. PCT/JP2021/027162, with English Translation. (4 pages).

* cited by examiner

*Primary Examiner* — Rochelle D Turchen
(74) *Attorney, Agent, or Firm* — WHDA, LLP

(57) ABSTRACT

An imaging device includes a camera unit and a control unit. A first power source voltage is transferred from the control unit to the camera unit by a power source line and is input to the camera unit as a second power source voltage. The control unit measures a value of a voltage generated at a point connecting the power source line and the control unit. The voltage at the point is generated based on both the second power source voltage held in a capacitor of the camera unit and a resistance component of the power source line. The control unit calculates a resistance value of the power source line based on the measured value. The control unit adjusts a value of the first power source voltage based on the resistance value.

11 Claims, 8 Drawing Sheets

FIG. 3

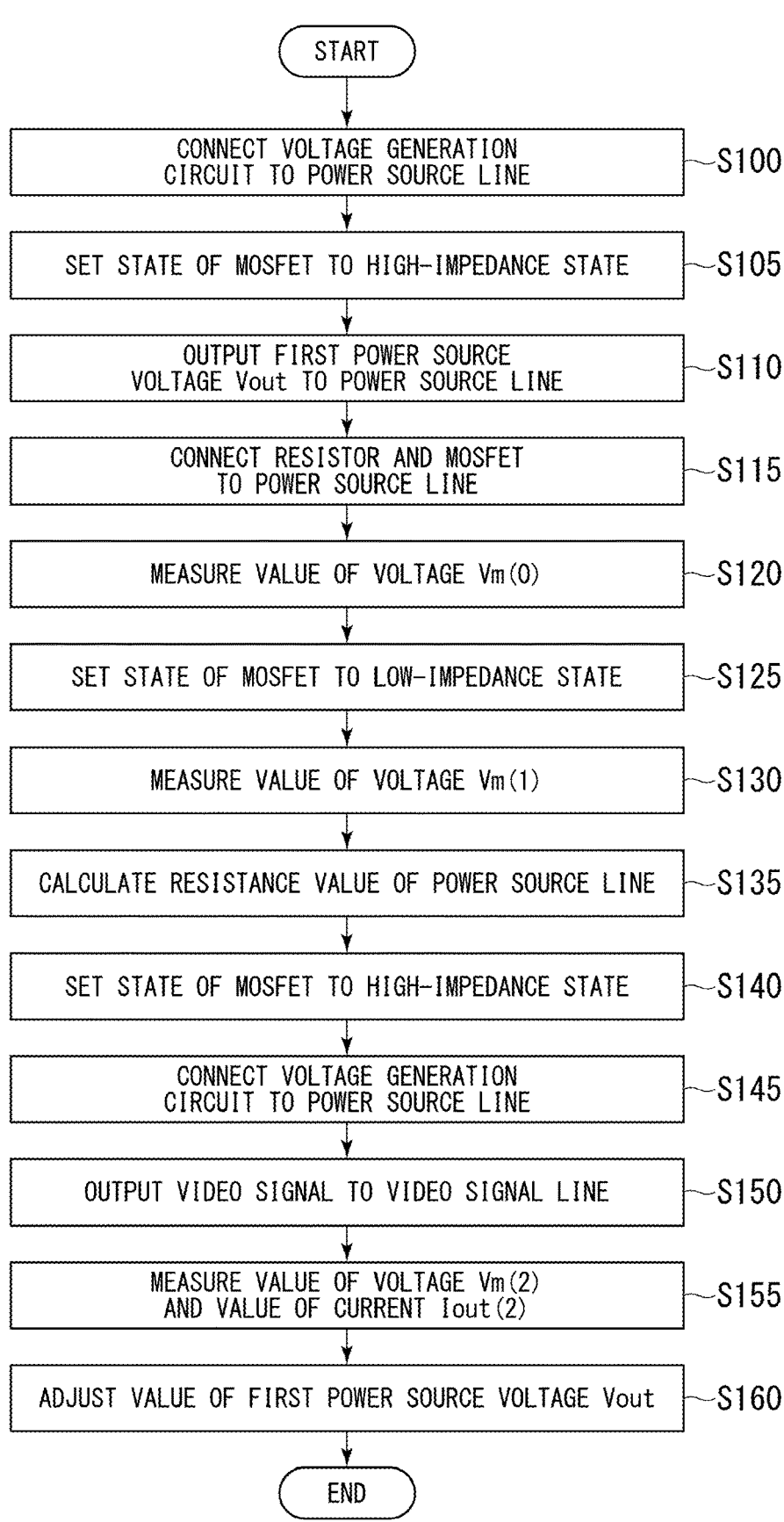

START

CONNECT VOLTAGE GENERATION
CIRCUIT TO POWER SOURCE LINE — S100

SET STATE OF MOSFET TO HIGH-IMPEDANCE STATE — S105

OUTPUT FIRST POWER SOURCE
VOLTAGE Vout TO POWER SOURCE LINE — S110

CONNECT RESISTOR AND MOSFET
TO POWER SOURCE LINE — S115

MEASURE VALUE OF VOLTAGE Vm(0) — S120

SET STATE OF MOSFET TO LOW-IMPEDANCE STATE — S125

MEASURE VALUE OF VOLTAGE Vm(1) — S130

CALCULATE RESISTANCE VALUE OF POWER SOURCE LINE — S135

SET STATE OF MOSFET TO HIGH-IMPEDANCE STATE — S140

CONNECT VOLTAGE GENERATION
CIRCUIT TO POWER SOURCE LINE — S145

OUTPUT VIDEO SIGNAL TO VIDEO SIGNAL LINE — S150

MEASURE VALUE OF VOLTAGE Vm(2)
AND VALUE OF CURRENT Iout(2) — S155

ADJUST VALUE OF FIRST POWER SOURCE VOLTAGE Vout — S160

END

FIG. 7

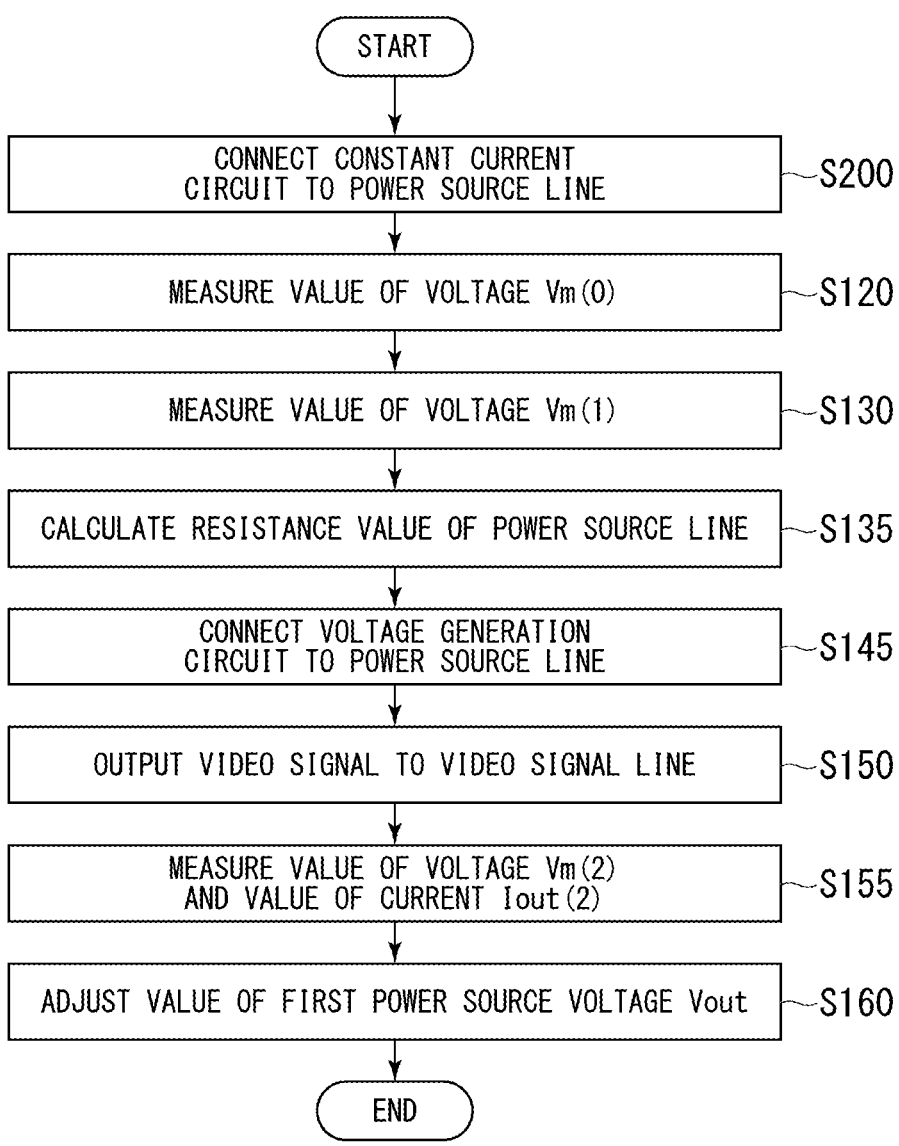

START

CONNECT CONSTANT CURRENT
CIRCUIT TO POWER SOURCE LINE — S200

MEASURE VALUE OF VOLTAGE Vm(0) — S120

MEASURE VALUE OF VOLTAGE Vm(1) — S130

CALCULATE RESISTANCE VALUE OF POWER SOURCE LINE — S135

CONNECT VOLTAGE GENERATION
CIRCUIT TO POWER SOURCE LINE — S145

OUTPUT VIDEO SIGNAL TO VIDEO SIGNAL LINE — S150

MEASURE VALUE OF VOLTAGE Vm(2)
AND VALUE OF CURRENT Iout(2) — S155

ADJUST VALUE OF FIRST POWER SOURCE VOLTAGE Vout — S160

END

FIG. 8

IMAGING DEVICE, ENDOSCOPE SYSTEM, CONTROL UNIT, AND IMAGING METHOD

The present application is a continuation application based on International Patent Application No. PCT/JP2021/027162 filed on Jul. 20, 2021, the content of which is incorporated herein by reference.

BACKGROUND OF THE INVENTION

Field of the Invention

The present invention relates to an imaging device, an endoscope system, a control unit, and an imaging method.

Description of Related Art

An endoscope system includes a scope (camera unit) and a control unit. The scope and the control unit are connected to each other by a power source cable. An imager is disposed in the distal end of the scope. The control unit outputs a first power source voltage used for driving the imager to the power source cable. The first power source voltage is transferred to the scope by the power source cable and is input to the scope as a second power source voltage. Due to an influence of a current flowing through the power source cable and the resistance value of the power source cable, a voltage drop is generated in the power source cable. Therefore, the second power source voltage in the imager is lower than the first power source voltage output from the control unit.

The amount of the current flowing through the power source cable changes in accordance with the driving state of the imager. Therefore, the control unit needs to output a first power source voltage having a high value to the power source cable in light of the voltage drop that occurs in accordance with a change of the current. However, a first power source voltage having a high value results in an increase of power consumption in the imager and an increase of the amount of heat generation in the power source cable. Therefore, it is required that the value of the second power source voltage in the imager be monitored and a first power source voltage having an optimal value be output to the power source cable.

A method of calculating the resistance value of the power source cable and calculating the value of the second power source voltage in accordance with the following Expression (1) has been considered in order to monitor the value of the second power source voltage.

$$Vcis = Vout - Rc*1c \qquad (1)$$

In Expression (1), a voltage value Vcis indicates the value of the second power source voltage, and a voltage value Vout indicates the value of the first power source voltage. In Expression (1), a resistance value Rc indicates the resistance value of the power source cable, and a current value Ic indicates the value of the current flowing through the power source cable.

The resistance value of the power source cable changes in accordance with an individual difference of the power source cable, passage of time, a change of temperature, and the like. In the above-described method, it is necessary to calculate the resistance value of the power source cable in order to properly control the first power source voltage.

A technique disclosed in Japanese Unexamined Patent Application, First Publication No. 2012-175484 provides a method of controlling a power source voltage that is provided from a power source device to a television camera. In the technique, a capacitor is charged in order to calculate a resistance value of a power source cable, and a voltage value of the capacitor is measured. A circuit in the television camera calculates the resistance value of the power source cable.

SUMMARY OF THE INVENTION

According to a first aspect of the present invention, an imaging device includes a camera unit and a control unit connected to each other by a power source line that transfers a first power source voltage. The first power source voltage transferred from the control unit by the power source line is input to the camera unit as a second power source voltage. The camera unit includes an image sensor and a capacitor. The image sensor is configured to generate a video signal by using the second power source voltage. The capacitor is configured to hold the second power source voltage. The control unit includes a voltage generation circuit, a voltage measurement circuit, a resistance calculation circuit, and a voltage adjustment circuit. The voltage generation circuit is configured to generate the first power source voltage and output the generated first power source voltage to the power source line. The voltage measurement circuit is configured to measure a value of a voltage generated at a point connecting the power source line and the control unit. The voltage at the point is generated based on both the second power source voltage held in the capacitor and a resistance component of the power source line. The resistance calculation circuit is configured to calculate a resistance value of the power source line based on the value measured by the voltage measurement circuit. The voltage adjustment circuit is configured to adjust a value of the first power source voltage by controlling the voltage generation circuit based on the resistance value calculated by the resistance calculation circuit.

According to a second aspect of the present invention, in the first aspect, the control unit may further include a resistor electrically connected to the power source line. A value of a current flowing through the resistor in a first period may be smaller than a value of a current flowing through the resistor in a second period different from the first period. The resistance calculation circuit may be configured to calculate the resistance value of the power source line based on a value of the second power source voltage in the first period, the value measured by the voltage measurement circuit in the second period, and a resistance value of the resistor.

According to a third aspect of the present invention, in the second aspect, the voltage measurement circuit may be configured to measure the value of the voltage generated at the point in the first period based on the second power source voltage held in the capacitor. The resistance calculation circuit may be configured to use the value measured by the voltage measurement circuit in the first period as the value of the second power source voltage in the first period.

According to a fourth aspect of the present invention, in the second aspect, the first period and the second period may be included in a blanking period of the image sensor.

According to a fifth aspect of the present invention, in the third aspect, the first period and the second period may be included in a blanking period of the image sensor.

According to a sixth aspect of the present invention, in the second aspect, the control unit may further include a transistor configured to enter a high-impedance state or a low-impedance state. The resistor may include a first terminal and a second terminal. The first terminal is electrically connected to the power source line. The second terminal is electrically connected to the transistor. A state of the transistor may be the high-impedance state in the first period. The state of the transistor may be the low-impedance state in the second period.

According to a seventh aspect of the present invention, in the first aspect, the camera unit and the control unit may be connected to each other by a video signal line that transfers the video signal. The voltage adjustment circuit may be configured to calculate a value of the second power source voltage in a video output period during which the video signal is output to the video signal line based on both the resistance value calculated by the resistance calculation circuit and a value of a current flowing through the power source line in the video output period. The voltage adjustment circuit may be configured to adjust the value of the first power source voltage such that the calculated value of the second power source voltage matches a target value.

According to an eighth aspect of the present invention, in the first aspect, the control unit may further include a constant current circuit configured to provide the power source line with a constant current used for charging the capacitor. The voltage measurement circuit may be configured to measure a first value of the voltage generated at the point at a first timing of a current output period during which the constant current is output to the power source line. The voltage measurement circuit may be configured to measure a second value of the voltage generated at the point at a second timing of the current output period. The second timing may be different from the first timing. The resistance calculation circuit may be configured to calculate the resistance value based on the first value and the second value.

According to a ninth aspect of the present invention, an endoscope system includes a scope to be inserted into a living body and includes the imaging device. The camera unit is disposed in a distal end of the scope.

According to a tenth aspect of the present invention, a control unit is connected to a camera unit by a power source line that transfers a first power source voltage. The first power source voltage transferred from the control unit by the power source line is input to the camera unit as a second power source voltage used for driving an image sensor of the camera unit. The control unit includes a voltage generation circuit, a voltage measurement circuit, a resistance calculation circuit, and a voltage adjustment circuit. The voltage generation circuit is configured to generate the first power source voltage and output the generated first power source voltage to the power source line. The voltage measurement circuit is configured to measure a value of a voltage generated at a point connecting the power source line and the control unit. The voltage at the point is generated based on both the second power source voltage held in a capacitor of the camera unit and a resistance component of the power source line. The resistance calculation circuit is configured to calculate a resistance value of the power source line based on the value measured by the voltage measurement circuit. The voltage adjustment circuit is configured to adjust a value of the first power source voltage by controlling the voltage generation circuit based on the resistance value calculated by the resistance calculation circuit.

According to an eleventh aspect of the present invention, an imaging method is executed in an imaging device including a camera unit and a control unit connected to each other by a power source line that transfers a first power source voltage. The first power source voltage transferred from the control unit by the power source line is input to the camera unit as a second power source voltage used for driving an image sensor of the camera unit. The imaging method includes a voltage output step, a voltage measurement step, a resistance calculation step, and a voltage adjustment step. In the voltage output step, a voltage generation circuit of the control unit generates the first power source voltage and outputs the generated first power source voltage to the power source line. In the voltage measurement step, a voltage measurement circuit of the control unit measures a value of a voltage generated at a point connecting the power source line and the control unit. The voltage at the point is generated based on both the second power source voltage held in a capacitor of the camera unit and a resistance component of the power source line. In the resistance calculation step, a resistance calculation circuit of the control unit calculates a resistance value of the power source line based on the value measured by the voltage measurement circuit. In the voltage adjustment step, a voltage adjustment circuit of the control unit adjusts a value of the first power source voltage by controlling the voltage generation circuit based on the resistance value calculated by the resistance calculation circuit.

BRIEF DESCRIPTION OF THE DRAWINGS

FIG. 3 is a flow chart showing a procedure of an operation of the endoscope system according to the first embodiment of the present invention.

FIG. 7 is a flow chart showing a procedure of an operation of the endoscope system according to the second embodiment of the present invention.

FIG. 8 is a timing chart showing a change of a voltage in the endoscope system according to the second embodiment of the present invention.

DETAILED DESCRIPTION OF THE INVENTION

Hereinafter, embodiments of the present invention will be described with reference to the drawings. Each of the embodiments will be described in detail by using an endoscope system as an example of an imaging device.

First Embodiment

Figure 1:
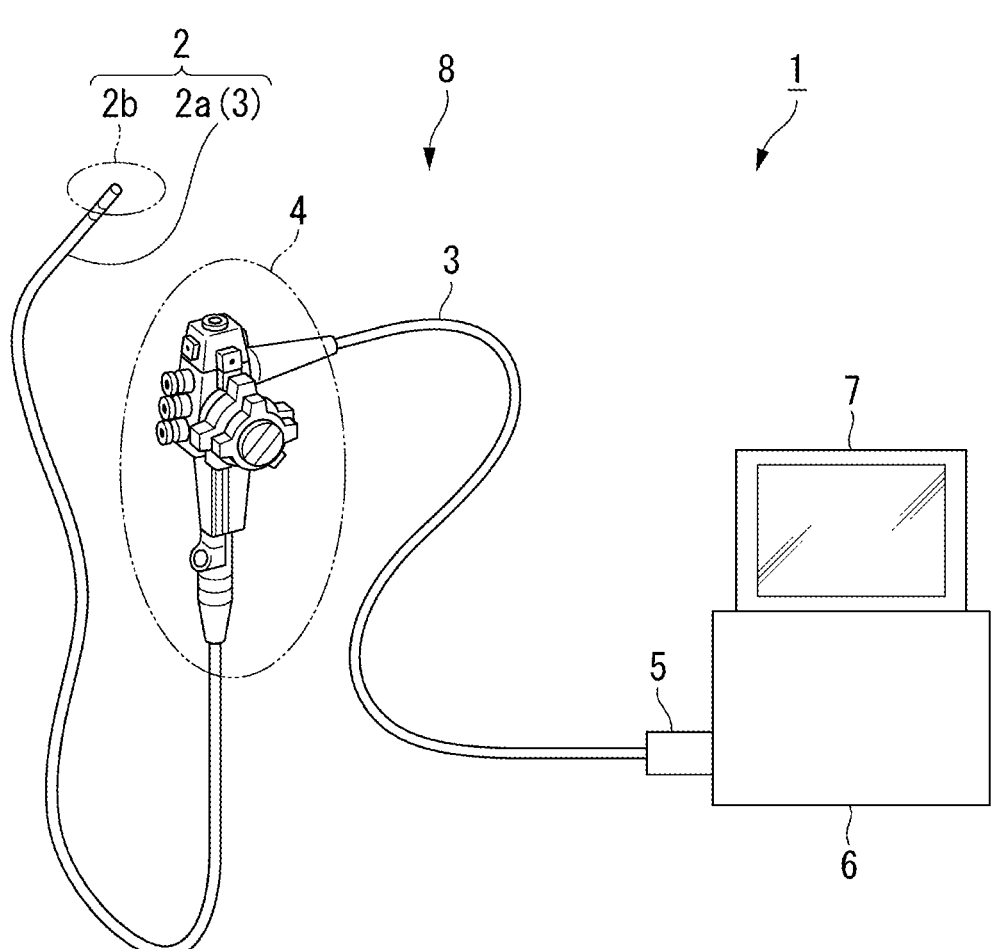
FIG. 1 is a schematic diagram showing a configuration of an endoscope system according to a first embodiment of the present invention.

FIG. 1 shows a configuration of an endoscope system 1 according to a first embodiment of the present invention. The endoscope system 1 shown in FIG. 1 includes an endoscope insertion unit 2, a transmission cable 3, an operation unit 4, a connector unit 5, a control unit 6, and a display device 7. The endoscope insertion unit 2, the transmission cable 3, the operation unit 4, and the connector unit 5 constitute a scope 8.

Figure 2:
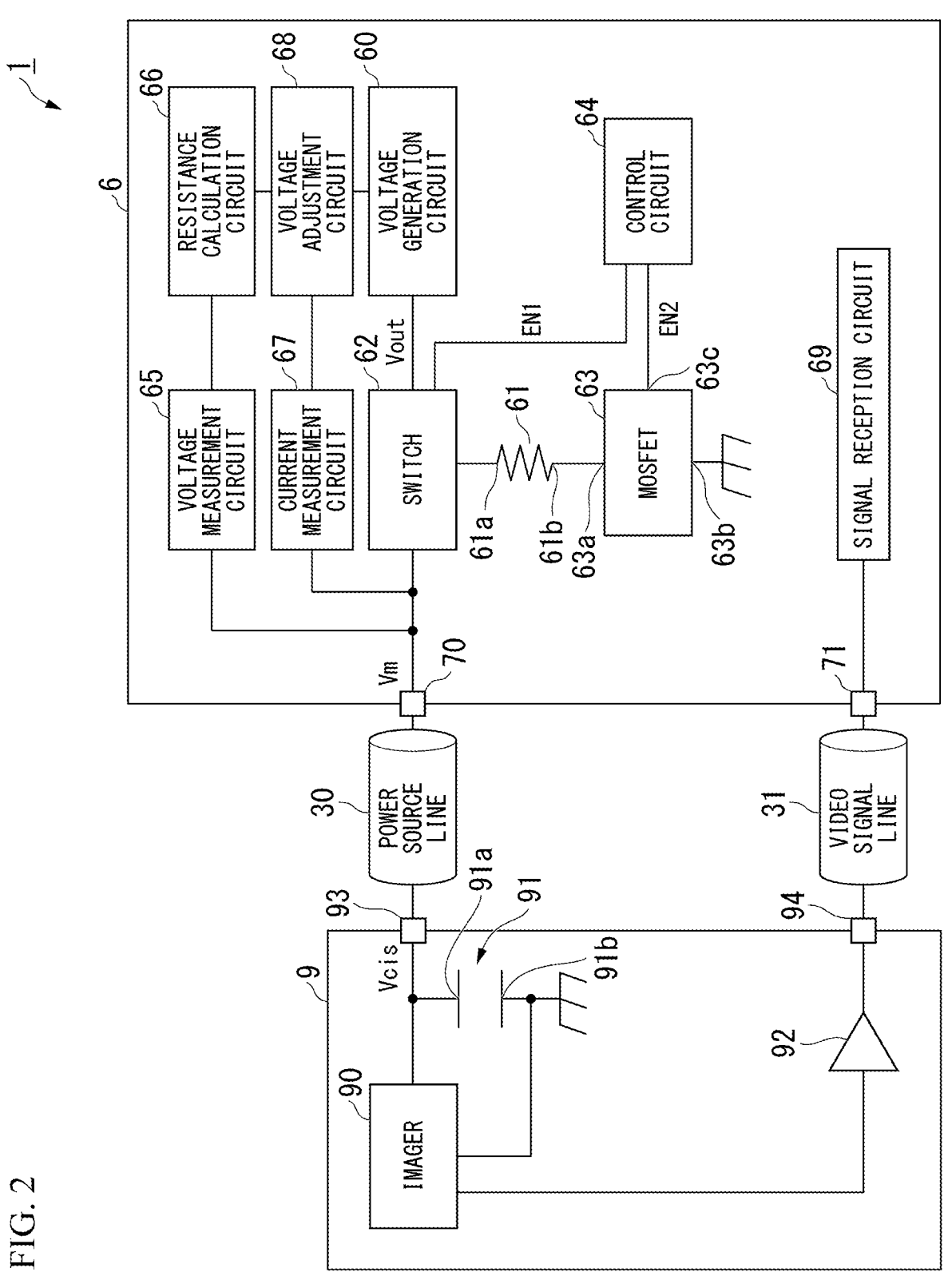
FIG. 2 is a block diagram showing a configuration of the endoscope system according to the first embodiment of the present invention.

The endoscope insertion unit 2 includes an insertion unit 2*a*. The insertion unit 2*a* is part of the transmission cable 3. The insertion unit 2*a* is to be inserted inside a living body, which is a subject. The endoscope insertion unit 2 generates a video signal by imaging the inside of the subject. The endoscope insertion unit 2 outputs the generated video signal to the control unit 6. A camera unit 9 shown in FIG. 2 is disposed in a distal end 2*b* of the insertion unit 2*a*. In the insertion unit 2*a*, the operation unit 4 is connected to the proximal end part opposite the distal end 2*b*. The operation unit 4 receives various operations for the endoscope insertion unit 2 from a user.

The transmission cable 3 connects the camera unit 9 and the connector unit 5. The video signal generated by the camera unit 9 is output to the connector unit 5 via the transmission cable 3.

The connector unit 5 is connected to the endoscope insertion unit 2 and the control unit 6. The connector unit 5 performs predetermined processing on the video signal output from the endoscope insertion unit 2. The connector unit 5 outputs the video signal to the control unit 6.

The control unit 6 performs image processing on the video signal output from the connector unit 5. Furthermore, the control unit 6 centrally controls the entire endoscope system 1.

The display device 7 displays a video based on the video signal processed by the control unit 6. In addition, the display device 7 displays various kinds of information related to the endoscope system 1.

FIG. 2 shows an internal configuration of the endoscope system 1. The endoscope system 1 shown in FIG. 2 includes the camera unit 9 and the control unit 6. The camera unit 9 is disposed in the distal end 2*b* of the scope 8. The operation unit 4, the connector unit 5, and the display device 7 are not shown in FIG. 2. The transmission cable 3 shown in FIG. 1 includes a power source line 30 and a video signal line 31 shown in FIG. 2.

The endoscope system 1 includes a light source device that generates illumination light emitted to the subject. The light source device is not shown in FIG. 2.

The camera unit 9 includes an imager 90, a capacitor 91 (capacitance element), a buffer 92, a power source terminal 93, and a video terminal 94. At least one of the capacitor 91, the buffer 92, the power source terminal 93, and the video terminal 94 may be disposed in the imager 90.

The control unit 6 includes a voltage generation circuit 60, a resistor 61, a switch 62, a metal-oxide-semiconductor field-effect transistor (MOSFET) 63, a control circuit 64, a voltage measurement circuit 65, a resistance calculation circuit 66, a current measurement circuit 67, a voltage adjustment circuit 68, a signal reception circuit 69, a power source terminal 70, and a video terminal 71. All or part of the configuration of the control unit 6 shown in FIG. 2 may be disposed in the operation unit 4 or the connector unit 5.

A schematic configuration of the endoscope system 1 will be described. The camera unit 9 and the control unit 6 are connected to each other by the power source line 30 that transfers a first power source voltage Vout. The first power source voltage Vout transferred from the control unit 6 by the power source line 30 is input to the camera unit 9 as a second power source voltage Vcis. The imager 90 generates a video signal by using the second power source voltage Vcis. The capacitor 91 holds the second power source voltage Vcis. The voltage generation circuit 60 generates the first power source voltage Vout and outputs the generated first power source voltage Vout to the power source line 30. The voltage measurement circuit 65 measures a value of a voltage Vm generated at a point connecting the power source line 30 and the control unit 6 based on both the second power source voltage Vcis held in the capacitor 91 and a resistance component of the power source line 30. The resistance calculation circuit 66 calculates the resistance value of the power source line 30 based on the value measured by the voltage measurement circuit 65. The voltage adjustment circuit 68 adjusts the value of the first power source voltage Vout based on the resistance value calculated by the resistance calculation circuit 66.

A detailed configuration of the endoscope system 1 will be described. For example, the voltage generation circuit 60 is a voltage regulator. The voltage generation circuit 60 generates the first power source voltage Vout, which is a direct-current (DC) voltage.

The voltage generation circuit 60 is connected to the switch 62. The switch 62 is connected to the power source terminal 70. The first power source voltage Vout generated by the voltage generation circuit 60 is input to the power source terminal 70 via the switch 62. The power source terminal 70 is connected to the power source line 30. The power source terminal 70 is disposed at a point connecting the power source line 30 and the control unit 6. The power source terminal 70 outputs the first power source voltage Vout to the power source line 30. The power source line 30 is a signal line disposed in the transmission cable 3. The power source line 30 transfers the first power source voltage Vout output from the power source terminal 70 to the camera unit 9.

The power source terminal 93 is connected to the power source line 30. The power source terminal 93 is disposed at a point connecting the power source line 30 and the camera unit 9. The first power source voltage Vout transferred by the power source line 30 is input to the power source terminal 93. The power source terminal 93 outputs the first power source voltage Vout to each circuit in the camera unit 9 as the second power source voltage Vcis. The second power source voltage Vcis is a power source voltage transferred to the camera unit 9 by the power source line 30 and is a voltage on a path from the power source terminal 93 to the imager 90 or a first terminal 91*a* of the capacitor 91. A voltage drop is generated due to the DC resistance of the power source line 30, and the second power source voltage Vcis is attenuated. Therefore, the value of the second power source voltage Vcis is smaller than that of the first power source voltage Vout in the control unit 6.

The capacitor 91 includes the first terminal 91*a* and a second terminal 91*b*. The first terminal 91*a* is connected to the imager 90 and the power source terminal 93. A ground voltage is input to the second terminal 91*b*. The second power source voltage Vcis output from the power source terminal 93 is input to the first terminal 91*a*. The capacitor 91 is charged by using the second power source voltage Vcis and holds the second power source voltage Vcis. For example, the capacitance value of the capacitor 91 ranges from several nF to several μF.

The imager 90 is an image sensor such as a complementary metal-oxide semiconductor (CMOS) sensor. The imager 90 includes a plurality of pixels and is driven based on the second power source voltage Vcis. The imager 90 generates a video signal having a voltage generated based on the second power source voltage Vcis. The imager 90 outputs the video signal to the buffer 92 in a video output period.

The buffer 92 is connected to the imager 90 and the video terminal 94. The video signal output from the imager 90 is input to the buffer 92. The buffer 92 outputs the video signal to the video terminal 94 in the video output period.

The video terminal 94 is connected to the video signal line 31. The video signal output from the buffer 92 is input to the video terminal 94. The video terminal 94 outputs the video signal to the video signal line 31. The video signal line 31 is a signal line disposed in the transmission cable 3. The video signal line 31 transfers the video signal output from the video terminal 94 to the control unit 6.

The video terminal 71 is connected to the video signal line 31. The video signal transferred by the video signal line 31 is input to the video terminal 71. The signal reception circuit 69 is connected to the video terminal 71. The signal reception circuit 69 receives the video signal input to the video terminal 71 in the video output period.

The switch 62 is connected to the power source terminal 70, the voltage generation circuit 60, and the resistor 61. The state of the switch 62 becomes either a first state or a second state. The state of the switch 62 can switch between the first state and the second state.

The state of the switch 62 is set to the first state in order to charge the capacitor 91. When the state of the switch 62 is the first state, the switch 62 connects the power source terminal 70 and the voltage generation circuit 60 to each other and disconnects the power source terminal 70 and the resistor 61 from each other. At this time, the first power source voltage Vout generated by the voltage generation circuit 60 is output to the power source line 30 via the switch 62 and the power source terminal 70. The capacitor 91 is charged by using the second power source voltage Vcis. The state of the switch 62 is set to the first state also in the video output period.

After the charge of the capacitor 91 is completed, the state of the switch 62 is set to the second state. When the state of the switch 62 is the second state, the switch 62 disconnects the power source terminal 70 and the voltage generation circuit 60 from each other and connects the power source terminal 70 and the resistor 61 to each other. At this time, a voltage input from the power source line 30 to the power source terminal 70 is input to the resistor 61 via the switch 62.

The resistor 61 includes a first terminal 61*a* and a second terminal 61*b*. The first terminal 61*a* is connected to the switch 62. The second terminal 61*b* is connected to the MOSFET 63.

The MOSFET 63 includes a drain terminal 63*a*, a source terminal 63*b*, and a gate terminal 63*c*. The drain terminal 63*a* is connected to the second terminal 61*b* of the resistor 61. The ground voltage is input to the source terminal 63*b*. The gate terminal 63*c* is connected to the control circuit 64.

The state of the MOSFET 63 becomes either a high-impedance state or a low-impedance state. The resistance value of the MOSFET 63 in the high-impedance state is larger than that of the MOSFET 63 in the low-impedance state. The MOSFET 63 can switch between the high-impedance state and the low-impedance state.

After the charge of the capacitor 91 is completed, the state of the switch 62 is set to the second state and the resistor 61 and the MOSFET 63 are electrically connected to the power source line 30. When the state of the switch 62 is the second state, the voltage of the power source terminal 70 is applied to the first terminal 61*a* of the resistor 61.

When the state of the switch 62 is the second state and the state of the MOSFET 63 is the high-impedance state, the state of the resistor 61 becomes the first state. At this time, no current flows through the resistor 61. When the state of the switch 62 is the second state and the state of the MOSFET 63 is the low-impedance state, the state of the resistor 61 becomes the second state. At this time, a current flows through the resistor 61 in accordance with the resistance value (conductive resistance value) of the power source line 30, the resistance value of the switch 62, the resistance value of the resistor 61, and the resistance value of the MOSFET 63. When the state of the resistor 61 is the first state, a significantly smaller current than that flowing through the resistor 61 in the second state may flow through the resistor 61.

The control circuit 64 outputs a control signal EN1 to the switch 62 and outputs a control signal EN2 to the gate terminal 63*c* of the MOSFET 63. The control circuit 64 controls the state of the switch 62 based on the control signal EN1 and controls the state of the MOSFET 63 based on the control signal EN2.

After the charge of the capacitor 91 is completed, the voltage measurement circuit 65 measures the value of the voltage Vm input from the power source line 30 to the power source terminal 70. The voltage Vm indicates a voltage on a path from the power source terminal 70 to the first terminal 61*a* of the resistor 61. The voltage measurement circuit 65 outputs the measured value to the resistance calculation circuit 66.

The resistance calculation circuit 66 calculates the resistance value of the power source line 30 based on the value of the voltage Vm measured by the voltage measurement circuit 65. The resistance calculation circuit 66 outputs the calculated resistance value to the voltage adjustment circuit 68.

The resistance calculation circuit 66 is a digital circuit including at least one of a processor and a logic circuit. For example, the processor is a central processing unit (CPU). For example, the logic circuit is at least one of an application-specific integrated circuit (ASIC) and a field-programmable gate array (FPGA). The resistance calculation circuit 66 may include one or a plurality of processors. The resistance calculation circuit 66 may include one or a plurality of logic circuits.

The resistance calculation circuit 66 may read a program and execute the read program. The program includes commands defining the operations of the resistance calculation circuit 66. In other words, the functions of the resistance calculation circuit 66 may be realized by software. The program may be transmitted from a computer storing the program to the endoscope system 1 through a transmission medium or transmission waves in a transmission medium. The "transmission medium" transmitting the program is a medium having a function of transmitting information. The medium having the function of transmitting information includes a network (communication network) such as the Internet and a communication circuit line (communication line) such as a telephone line. The program described above may realize some of the functions described above. In addition, the program described above may be a differential file (differential program). The functions described above may be realized by a combination of a program that has already been recorded in a computer and a differential program.

The current measurement circuit 67 measures a value of a current output to the power source line 30 via the power source terminal 70 in the video output period. The value indicates the current value of the power source line 30. The current measurement circuit 67 outputs the measured value to the voltage adjustment circuit 68.

The voltage adjustment circuit 68 calculates the value of the second power source voltage Vcis based on the resistance value of the power source line 30 and the current value of the power source line 30 in the video output period. The voltage adjustment circuit 68 adjusts the value of the first power source voltage Vout generated by the voltage generation circuit 60 by controlling the voltage generation circuit 60 based on the value of the second power source voltage Vcis. For example, the voltage adjustment circuit 68 includes a digital circuit that calculates the value of the second power source voltage Vcis and an analog circuit that controls the voltage generation circuit 60.

Figure 4:
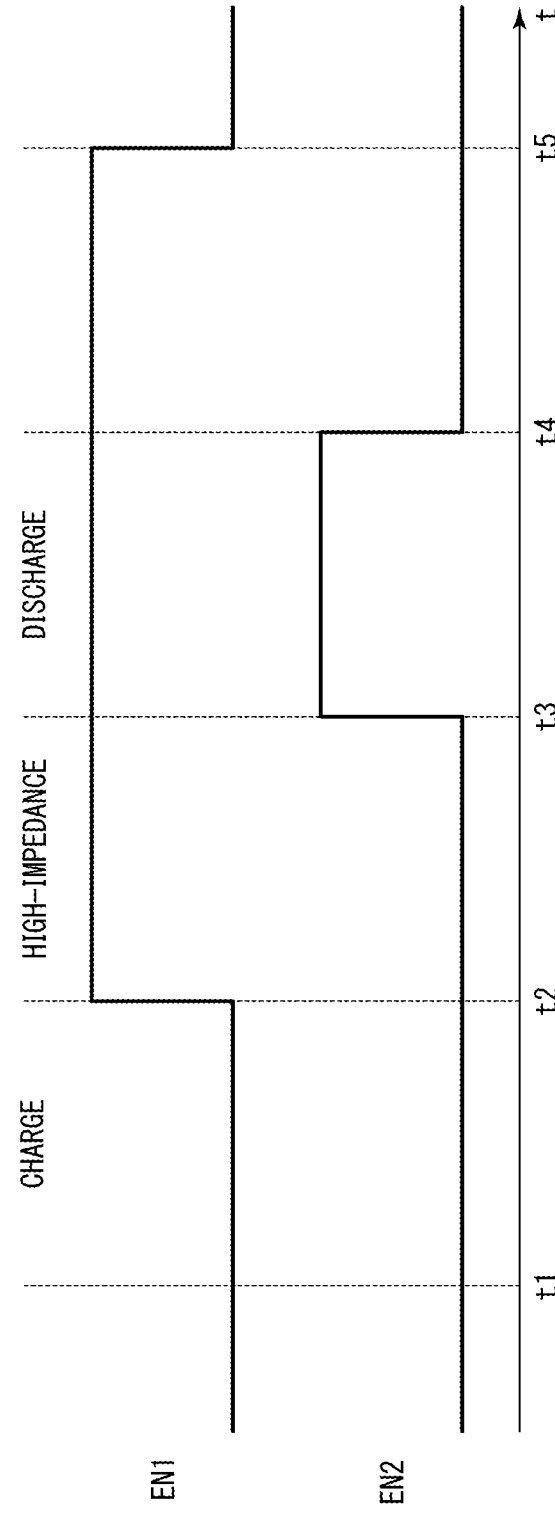
FIG. 4 is a timing chart showing waveforms of control signals in the endoscope system according to the first embodiment of the present invention.

FIG. 3 shows a procedure of an operation of the endoscope system 1. FIG. 4 shows waveforms of the control signal EN1 and the control signal EN2. The horizontal direction in FIG. 4 indicates time, and the vertical direction in FIG. 4 indicates a voltage value of each control signal. The operation of the endoscope system 1 will be described by using FIG. 3 and FIG. 4.

The control circuit 64 outputs the control signal EN1 having a low (L) level to the switch 62 and sets the state of the switch 62 to the first state. The switch 62 connects the power source terminal 70 and the voltage generation circuit 60 to each other and disconnects the power source terminal 70 and the resistor 61 from each other. Due to this, the voltage generation circuit 60 is electrically connected to the power source line 30 (Step S100).

After Step S100, the control circuit 64 outputs the control signal EN2 having the L level to the MOSFET 63 and sets the state of the MOSFET 63 to the high-impedance state (Step S105).

Before a time point t1 shown in FIG. 4, the voltage of each of the control signals EN1 and EN2 is the low (L) level. At this time, the state of the switch 62 is set to the first state. In addition, the state of the MOSFET 63 is set to the high-impedance state.

After Step S105, the voltage generation circuit 60 generates the first power source voltage Vout and outputs the generated first power source voltage Vout to the power source line 30 via the switch 62 and the power source terminal 70 (Step S110).

The first power source voltage Vout is transferred to the camera unit 9 by the power source line 30 and is input to the power source terminal 93 as the second power source voltage Vcis. The second power source voltage Vcis output from the power source terminal 93 is input to the capacitor 91. The capacitor 91 is charged by using the second power source voltage Vcis. For example, a period of about 160 μs is required until the charge of the capacitor 91 is completed. When the charge of the capacitor 91 is completed, the value of the second power source voltage Vcis is the same as that of the first power source voltage Vout.

After the charge of the capacitor 91 is completed, the control circuit 64 outputs the control signal EN1 having a high (H) level to the switch 62 at a time point t2 and sets the state of the switch 62 to the second state. The switch 62 disconnects the power source terminal 70 and the voltage generation circuit 60 from each other and connects the power source terminal 70 and the resistor 61 to each other. Due to this, the resistor 61 and the MOSFET 63 are electrically connected to the power source line 30 (Step S115).

After Step S115, the voltage measurement circuit 65 measures the value of the voltage Vm(0) of the power source terminal 70 (Step S120).

Since the state of the MOSFET 63 is the high-impedance state, no current flows through the power source line 30, the resistor 61, or the MOSFET 63. Therefore, the value of the voltage Vm(0) is the same as that of the second power source voltage Vcis(0) held in the capacitor 91.

After Step S120, the control circuit 64 outputs the control signal EN2 having the H level to the MOSFET 63 at a time point t3 and sets the state of the MOSFET 63 to the low-impedance state (Step S125). Due to this, the discharge of the capacitor 91 is started.

Immediately after the state of the MOSFET 63 is set to the low-impedance state, the voltage measurement circuit 65 measures the value of the voltage Vm(1) of the power source terminal 70 (Step S130).

When the discharge of the capacitor 91 is started, the value of the second power source voltage Vcis(1) held in the capacitor 91 is the same as the above-described value of the second power source voltage Vcis(0). For example, the value of the second power source voltage Vcis(1) is almost the same as that of the second power source voltage Vcis(0) in a period from a timing at which the discharge of the capacitor 91 is started to a timing at which 1 μs passes.

After the discharge of the capacitor 91 is started, the second power source voltage Vcis(1) is divided by a first resistor and a second resistor. The first resistor contains a resistance component of the power source line 30. The second resistor contains a resistance component of the switch 62, the resistor 61, and a resistance component (ON resistance) of the MOSFET 63 in the low-impedance state. A voltage obtained by dividing the second power source voltage Vcis(1) is input to the power source terminal 70. The following Expression (2) indicates the value of the voltage Vm(1) of the power source terminal 70.

$$V_m(1) = \frac{R2}{R1 + R2} \times V_{cis}(1) \tag{2}$$

In Expression (2), a resistance value R1 indicates the value of the first resistor, and a resistance value R2 indicates the value of the second resistor. By solving Expression (2) regarding the resistance value R1, the following Expression (3) is obtained.

$$R1 = \left( \frac{V_{cis}(1)}{V_m(1)} - 1 \right) \times R2 \tag{3}$$

After Step S130, the resistance calculation circuit 66 calculates the resistance value R1 in accordance with Expression (3). In other words, the resistance calculation circuit 66 calculates the resistance value of the power source line 30 (Step S135).

The resistance value R2 in Expression (3) is known. As described above, the value of the second power source voltage Vcis(1) is the same as that of the second power source voltage Vcis(0), and the value of the voltage Vm(0) is the same as that of the second power source voltage Vcis(0). In other words, the value of the second power source voltage Vcis(1) is the same as that of the voltage Vm(0). The resistance calculation circuit 66 calculates the resistance value of the power source line 30 based on the values of the voltages Vm(0) and Vm(1) measured by the voltage measurement circuit 65 and the resistance value R2.

After Step S135, the control circuit 64 outputs the control signal EN2 having the L level to the MOSFET 63 at a time point t4 and sets the state of the MOSFET 63 to the high-impedance state (Step S140).

After Step S140, the control circuit 64 outputs the control signal EN1 having the L level to the switch 62 at a time point t5 and sets the state of the switch 62 to the first state. The switch 62 connects the power source terminal 70 and the voltage generation circuit 60 to each other and disconnects the power source terminal 70 and the resistor 61 from each other. Due to this, the voltage generation circuit 60 is electrically connected to the power source line 30 (Step S145).

The voltage generation circuit 60 generates the first power source voltage Vout and outputs the generated first power source voltage Vout to the power source line 30 via the switch 62 and the power source terminal 70. The first power source voltage Vout is transferred to the camera unit 9 by the power source line 30 and is input to the power source terminal 93 as the second power source voltage Vcis. The second power source voltage Vcis output from the power source terminal 93 is input to the imager 90.

After Step S145, the imager 90 outputs the video signal to the buffer 92 in the video output period. The buffer 92 outputs the video signal to the video signal line 31 via the video terminal 94 (Step S150).

The video signal is transferred to the control unit 6 by the video signal line 31 and is input to the video terminal 71. The signal reception circuit 69 receives the video signal input to the video terminal 71. The capacitor 91 is charged by using the second power source voltage Vcis in the video output period. The capacitor 91 stabilizes the second power source voltage Vcis provided to the imager 90.

When the video signal is output to the video signal line 31, the voltage measurement circuit 65 measures the value of the voltage Vm(2) of the power source terminal 70. In addition, the current measurement circuit 67 measures the value of the current Iout(2) of the power source line 30 (Step S155).

After Step S155, the voltage adjustment circuit 68 calculates the value of the second power source voltage Vcis(2) based on the resistance value of the power source line 30, the value of the voltage Vm(2), and the value of the current Iout(2). The voltage adjustment circuit 68 adjusts the value of the first power source voltage Vout generated by the voltage generation circuit 60 by controlling the voltage generation circuit 60 based on the value of the second power source voltage Vcis(2) (Step S160).

Specifically, the voltage adjustment circuit 68 calculates the value of the second power source voltage Vcis(2) in accordance with the following Expression (4).

$$Vcis(2)=Vm(2)-Rc*Iout(2) \qquad (4)$$

A resistance value Rc in Expression (4) indicates the resistance value of the power source line 30 calculated in Step S135. The voltage adjustment circuit 68 adjusts the value of the first power source voltage Vout such that the value of the second power source voltage Vcis(2) matches a target value. For example, a predetermined target value is 3.3 V.

Steps S100 to S145 are executed before the imager 90 is activated. After the video output period, the imager 90 stops the output of the video signal in a blanking period. At this time, the capacitor 91 holds the second power source voltage Vcis. Steps S115 to S145 may be executed in the blanking period. The imager 90 may include a circuit used for holding the second power source voltage Vcis in the blanking period. For example, the length of the blanking period is 1 ms to 50 ms.

The value of the voltage Vm(0) is the same as that of the second power source voltage Vcis(0). In addition, the value of the second power source voltage Vcis(0) is the same as that of the first power source voltage Vout. In other words, the value of the voltage Vm(0) is the same as that of the first power source voltage Vout. Therefore, a known voltage value may be used as the value of the voltage Vm(0). Accordingly, Step S120 does not need to be executed.

An imaging method according to each aspect of the present invention includes a voltage output step, a voltage measurement step, a resistance calculation step, and a voltage adjustment step. The voltage generation circuit 60 generates the first power source voltage Vout and outputs the generated first power source voltage Vout to the power source line 30 in the voltage output step (Step S110). The voltage measurement circuit 65 measures the value of the voltage Vm(1) generated at a point connecting the power source line 30 and the control unit 6 based on both the second power source voltage Vcis(1) held in the capacitor 91 and a resistance component of the power-source line 30 in the voltage measurement step (Step S130). The resistance calculation circuit 66 calculates the resistance value Rc of the power source line 30 based on the value measured by the voltage measurement circuit 65 in the resistance calculation step (Step S135). The voltage adjustment circuit 68 adjusts the value of the first power source voltage Vout based on the resistance value Rc calculated by the resistance calculation circuit 66 in the voltage adjustment step (Step S160).

Each aspect of the present invention may include the following modified example. The resistor 61 is electrically connected to the power source line 30. The value of a current flowing through the resistor 61 in a first period is smaller than that of a current flowing through the resistor 61 in a second period. The resistance calculation circuit 66 calculates the resistance value Rc of the power source line 30 based on the value of the second power source voltage Vcis(0) in the first period, the value of the voltage Vm(1) measured by the voltage measurement circuit 65 in the second period, and the resistance value of the resistor 61.

The above-described first period is a period from the time point t2 to the time point t3 shown in FIG. 4. The above-described second period is a period from the time point t3 to the time point t4 shown in FIG. 4. The first period and the second period may be included in the blanking period of the imager 90.

Each aspect of the present invention may include the following modified example. The voltage measurement circuit 65 measures the value of the voltage Vm(0) generated at the point connecting the power source line 30 and the control unit 6 in the first period based on the second power source voltage Vcis(0) held in the capacitor 91. The resistance calculation circuit 66 uses the value of the voltage Vm(0) measured by the voltage measurement circuit 65 in the first period as the value of the second power source voltage Vcis(0) in the first period.

Each aspect of the present invention may include the following modified example. The MOSFET 63 enters the high-impedance state or the low-impedance state. The resistor 61 includes the first terminal 61a electrically connected to the power source line 30 and the second terminal 61b electrically connected to the MOSFET 63. The state of the MOSFET 63 is the high-impedance state in the first period. The state of the MOSFET 63 is the low-impedance state in the second period.

Each aspect of the present invention may include the following modified example. The camera unit 9 and the control unit 6 are connected to each other by the video signal line 31 that transfers the video signal. The voltage adjustment circuit 68 calculates the value of the second power source voltage Vcis(2) in the video output period during which the video signal is output to the video signal line 31 based on the resistance value Rc calculated by the resistance calculation circuit 66 and the value of the current Iout(2) flowing through the power source line 30 in the video output period. The voltage adjustment circuit 68 adjusts the value of the first power source voltage Vout such that the calculated value of the second power source voltage Vcis(2) matches a target value.

In the first embodiment, the resistance calculation circuit 66 calculates the resistance value of the power source line 30 based on the value of the voltage generated at the point connecting the power source line 30 and the control unit 6. Therefore, the configuration of the camera unit 9 can be simplified, compared to a case in which a circuit that calculates the resistance value of the power source line 30 is disposed in the camera unit 9.

The video signal line 31 is not used for monitoring the second power source voltage Vcis. The resistance calculation circuit 66 can calculate the resistance value of the power source line 30 without being affected by the resistance value of the video signal line 31.

Modified Example of First Embodiment

Figure 5:
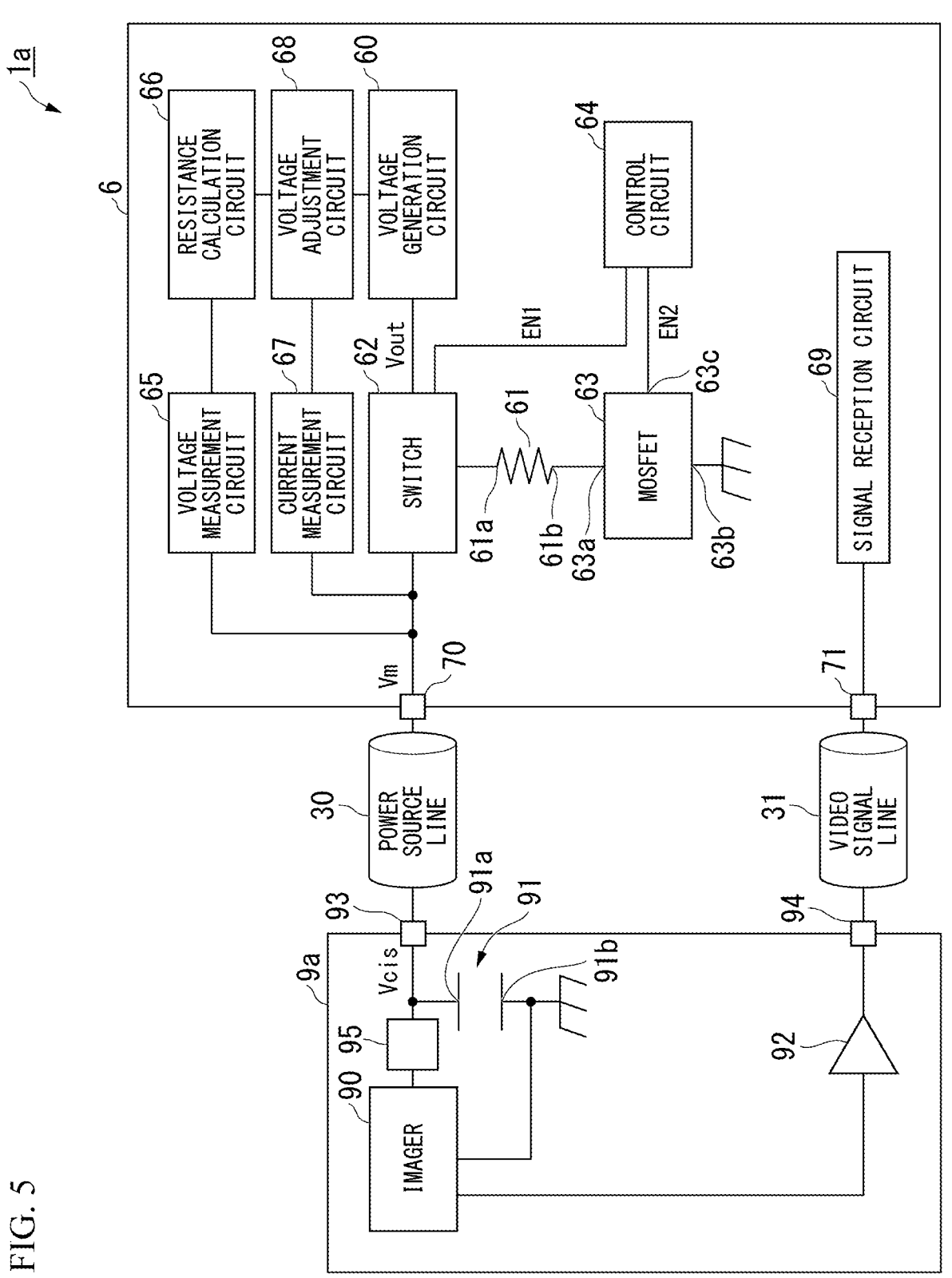
FIG. 5 is a block diagram showing a configuration of an endoscope system according to a modified example of the first embodiment of the present invention.

FIG. 5 shows a configuration of an endoscope system 1a according to a modified example of the first embodiment of the present invention. The same configuration as that shown in FIG. 2 will not be described.

The camera unit 9 shown in FIG. 2 is changed to a camera unit 9a. The camera unit 9a includes an imager 90, a capacitor 91, a buffer 92, a power source terminal 93, a video terminal 94, and a switch 95.

The switch 95 is connected to the imager 90, the capacitor 91, and the power source terminal 93. The state of the switch 95 becomes either an ON state or an OFF state. The state of the switch 95 can switch between the ON state and the OFF state.

Before the charge of the capacitor 91 is started, the state of the switch 95 is set to the OFF state. When the state of the switch 95 is the OFF state, the switch 95 disconnects the imager 90 and the capacitor 91 from each other and disconnects the imager 90 and the power source terminal 93 from each other. After the charge of the capacitor 91 is completed, the state of the switch 62 is set to the second state and the state of the MOSFET 63 is set to the low-impedance state.

The state of the switch 95 is set to the ON state in the video output period. When the state of the switch 95 is the ON state, the switch 95 connects the imager 90 and the capacitor 91 to each other and connects the imager 90 and the power source terminal 93 to each other. The state of the switch 95 may be set to the ON state before the charge of the capacitor 91 is completed. The state of the switch 95 may be set to the OFF state after the charge of the capacitor 91 is completed.

When the capacitor 91 is discharged, the imager 90 is not connected to the power source line 30. Therefore, an influence of both the parasitic capacitance of the imager 90 and the impedance of the imager 90 is eliminated.

Second Embodiment

Figure 6:
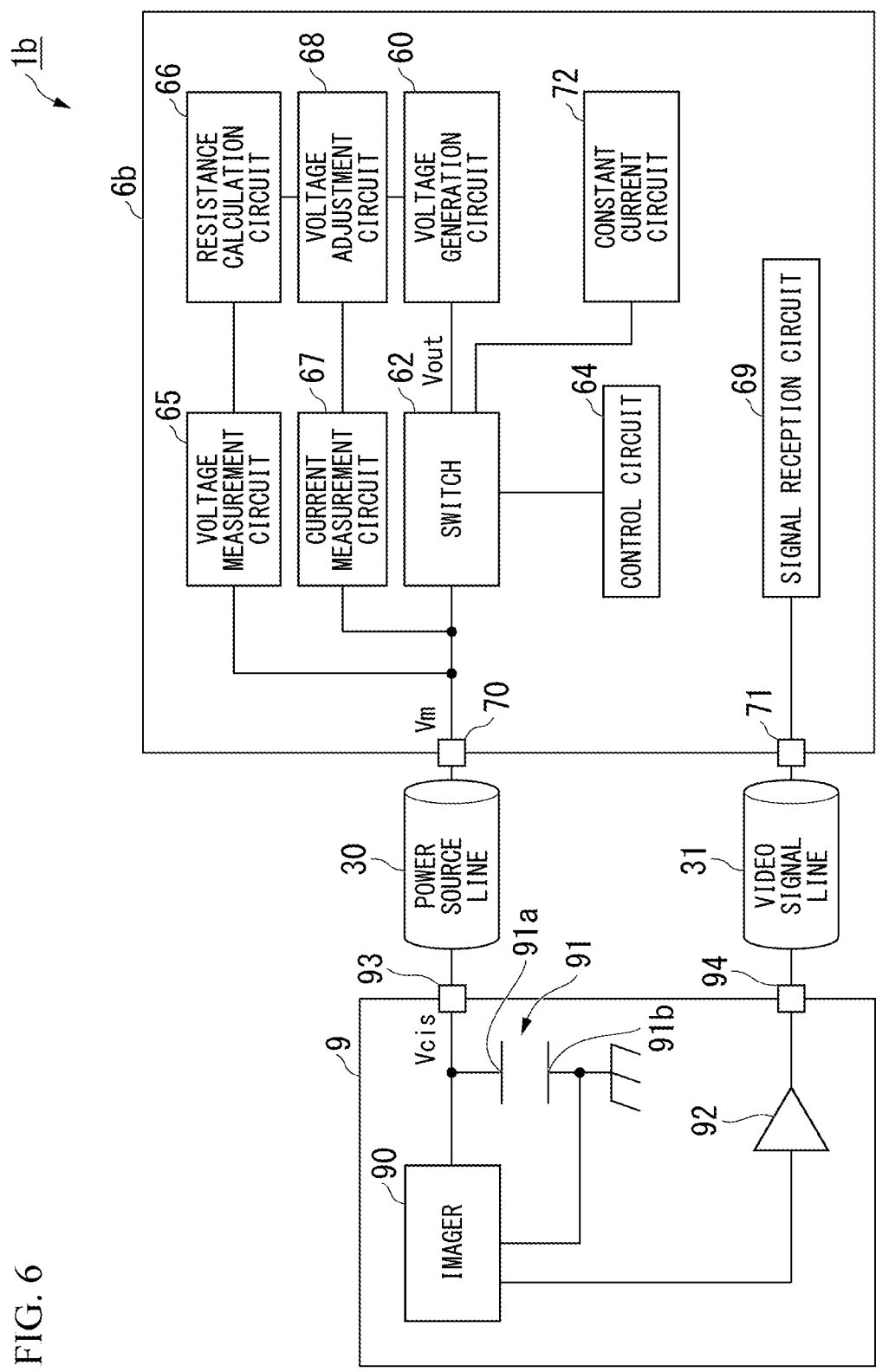
FIG. 6 is a block diagram showing a configuration of an endoscope system according to a second embodiment of the present invention.

FIG. 6 shows a configuration of an endoscope system 1b according to a second embodiment of the present invention. The same configuration as that shown in FIG. 2 will not be described.

The control unit 6 shown in FIG. 2 is changed to a control unit 6b. The control unit 6b includes a voltage generation circuit 60, a switch 62, a control circuit 64, a voltage measurement circuit 65, a resistance calculation circuit 66, a current measurement circuit 67, a voltage adjustment circuit 68, a signal reception circuit 69, a power source terminal 70, a video terminal 71, and a constant current circuit 72. All or part of the configuration of the control unit 6b shown in FIG. 6 may be disposed in the operation unit 4 or the connector unit 5.

The constant current circuit 72 is connected to the switch 62. The constant current circuit 72 generates a constant current used for charging the capacitor 91.

The switch 62 is connected to the power source terminal 70, the voltage generation circuit 60, and the constant current circuit 72. The state of the switch 62 becomes either a first state or a second state. The switch 62 can switch between the first state and the second state.

The state of the switch 62 is set to the second state in order to charge the capacitor 91. When the state of the switch 62 is the second state, the switch 62 disconnects the power source terminal 70 and the voltage generation circuit 60 from each other and connects the power source terminal 70 and the constant current circuit 72 to each other. At this time, the constant current is output from the constant current circuit 72 to the power source line 30. The constant current is transferred to the camera unit 9 via the power source line 30. The capacitor 91 is charged by using the constant current.

After the charge of the capacitor 91 is completed, the state of the switch 62 is set to the first state. When the state of the switch 62 is the first state, the switch 62 connects the power source terminal 70 and the voltage generation circuit 60 to each other and disconnects the power source terminal 70 and the constant current circuit 72 from each other. At this time, the first power source voltage Vout generated by the voltage generation circuit 60 is output to the power source line 30 via the switch 62 and the power source terminal 70.

While the capacitor 91 is charged, the voltage measurement circuit 65 measures the value of the voltage input from the power source line 30 to the power source terminal 70. The voltage measurement circuit 65 measures the value of the voltage at a first timing and a second timing different from each other. The voltage measurement circuit 65 outputs the measured value to the resistance calculation circuit 66.

Figure 8:
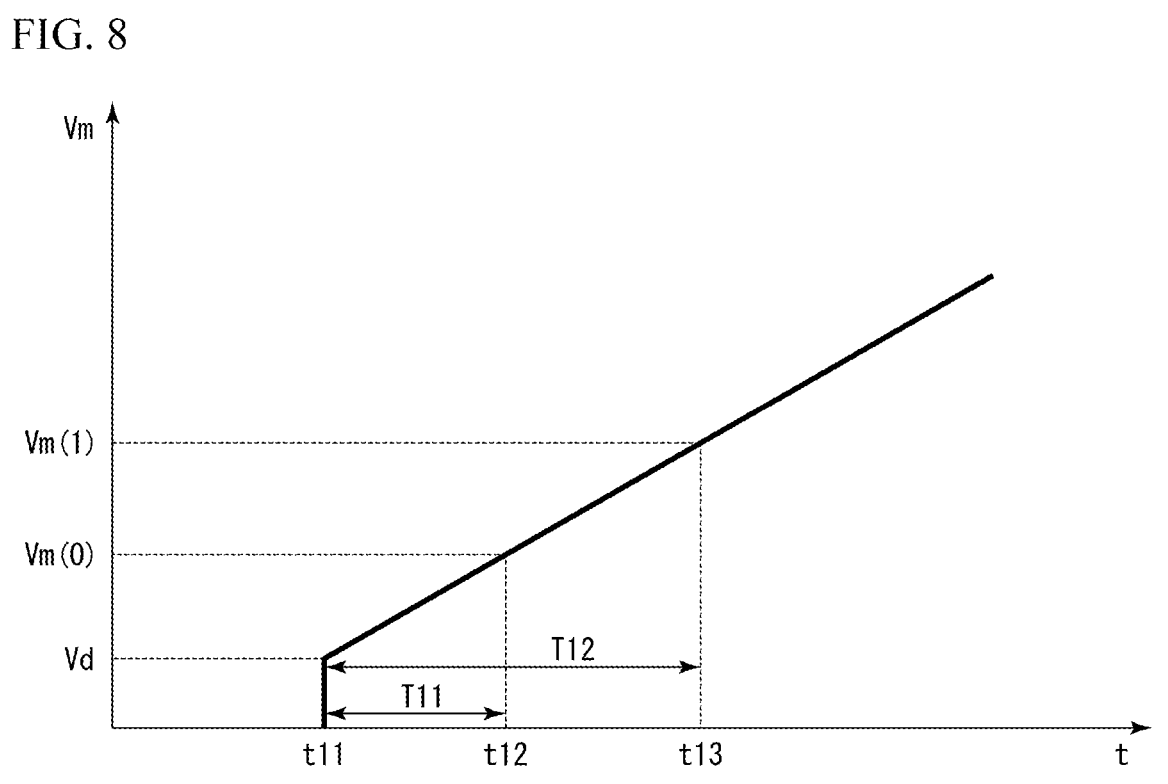

FIG. 7 shows a procedure of an operation of the endoscope system 1b. FIG. 8 shows a change of the voltage Vin of the power source terminal 70. The horizontal direction in FIG. 8 indicates time, and the vertical direction in FIG. 8 indicates the voltage value of the voltage Vm. The operation of the endoscope system 1b will be described by using FIG. 7 and FIG. 8.

The control circuit 64 sets the state of the switch 62 to the second state. The switch 62 disconnects the power source terminal 70 and the voltage generation circuit 60 from each other and connects the power source terminal 70 and the constant current circuit 72 to each other. Due to this, the constant current circuit 72 is electrically connected to the power source line 30 (Step S200).

The state of the switch 62 is set to the second state at a time point t11 shown in FIG. 8. At this time, the constant current generated by the constant current circuit 72 is output to the power source line 30, and the charge of the capacitor 91 is started. A voltage drop is generated due to a DC resistance of the power source line 30 at the time point t11, and the voltage Vm has a value Vd in accordance with the voltage drop. Since the capacitor 91 is charged by using the constant current, the voltage Vm gradually increases. The slope of a change of the voltage Vm is constant.

After Step S200, the voltage measurement circuit 65 measures the value of the voltage Vm(0) of the power source terminal 70 at a time point t12 shown in FIG. 8 (Step S120). The value of the voltage Vm(0) is higher than that of the voltage Vd by a voltage that is in accordance with the amount of the electric charge accumulated in the capacitor 91 in a first period T11 from the time point t11 to the time point t12.

After Step S120, the voltage measurement circuit 65 measures the value of the voltage Vm(1) of the power source terminal 70 at a time point t13 shown in FIG. 8 (Step S130). The value of the voltage Vm(1) is higher than that of the voltage Vd by a voltage that is in accordance with the amount of the electric charge accumulated in the capacitor 91 in a second period T12 from the time point t11 to the time point t13. The second period T12 is longer than the first period T11.

The following Expression (5) indicates the value of the voltage Vm(0).

$$V_m(0) = \frac{I_c \times T11}{C_b} + R_c \times I_c \qquad (5)$$

A current value Ic in Expression (5) indicates the value of the constant current generated by the constant current circuit 72. The current value Ic is known. The current measurement circuit 67 may measure the current value Ic. A capacitance value Cb in Expression (5) indicates a known capacitance value of the capacitor 91. A resistance value Re in Expression (5) indicates the resistance value of the power source line 30.

The following Expression (6) indicates the value of the voltage Vm(1).

$$V_m(1) = \frac{I_c \times T12}{C_b} + R_c \times I_c \qquad (6)$$

By solving Expression (5) and Expression (6) regarding the resistance value Rc, the following Expression (7) is obtained.

$$V_m(0) \times T12 - V_m(1) \times T11 = \qquad (7)$$
$$\left( \frac{I_c \times T11}{C_b} + R_c \times I_c \right) \times T12 - \left( \frac{I_c \times T12}{C_b} + R_c \times I_c \right) \times T11$$
$$V_m(0) \times T12 - V_m(1) \times T11 = (T12 - T11) \times R_c \times I_c$$
$$R_c = \frac{V_m(0) \times T12 - V_m(1) \times T11}{(T12 - T11) \times I_c}$$

After Step S130, the resistance calculation circuit 66 calculates the resistance value Rc in accordance with Expression (7). In other words, the resistance calculation circuit 66 calculates the resistance value of the power source line 30 (Step S135).

After Step S135, the control circuit 64 sets the state of the switch 62 to the first state. The switch 62 connects the power source terminal 70 and the voltage generation circuit 60 to each other and disconnects the power source terminal 70 and the constant current circuit 72 from each other. Due to this, the voltage generation circuit 60 is electrically connected to the power source line 30 (Step S145).

The voltage generation circuit 60 generates the first power source voltage Vout and outputs the generated first power source voltage Vout to the power source line 30 via the switch 62 and the power source terminal 70. The first power source voltage Vout is transferred to the camera unit 9 by the power source line 30 and is input to the power source terminal 93 as the second power source voltage Vcis. The second power source voltage Vcis output from the power source terminal 93 is input to the imager 90.

After Step S145, Step S150, Step S155, and Step S160 are executed. Each step is the same as that shown in FIG. 3.

Steps S200 to S145 are executed before the imager 90 is activated. After the video output period, the imager 90 stops the output of the video signal in a blanking period. At this time, the capacitor 91 holds the second power source voltage Vcis. Steps S200 to S145 may be executed in the blanking period. In a case in which the capacitor 91 is charged by using the constant current in the blanking period, the voltage of the capacitor 91 is higher than the second power source voltage Vcis in the video output period.

Each aspect of the present invention may include the following modified example. The constant current circuit 72 provides the power source line 30 with a constant current used for charging the capacitor 91. The voltage measurement circuit 65 measures the value (first value) of the voltage Vm(0) generated at the point connecting the power source line 30 and the control unit 6b at a first timing (time point t12) of a current output period during which the constant current is output to the power source line 30. The voltage measurement circuit 65 measures the value (second value) of the voltage Vm(1) generated at the point at a second timing (time point t13) of the current output period. The second timing is different from the first timing. The resistance calculation circuit 66 calculates the resistance value Rc of the power source line 30 based on the first value and the second value.

In the second embodiment, the resistance calculation circuit 66 calculates the resistance value of the power source line 30 based on the value of the voltage generated at the point connecting the power source line 30 and the control unit 6b. Therefore, the configuration of the camera unit 9 can be simplified, compared to a case in which a circuit that calculates the resistance value of the power source line 30 is disposed in the camera unit 9.

The video signal line 31 is not used for monitoring the second power source voltage Vcis. The resistance calculation circuit 66 can calculate the resistance value of the power source line 30 without being affected by the resistance value of the video signal line 31.

Modified Example of Second Embodiment

A modified example of the second embodiment according to the present invention will be described. The resistance calculation circuit 66 calculates the resistance value Rc in accordance with a different expression from Expression (7) in the modified example of the second embodiment.

The constant current circuit 72 outputs a constant current having a first value Ic(0) to the power source line 30. Due to this, the charge of the capacitor 91 is started. When the first period T11 has passed from a timing at which the charge of the capacitor 91 is started, the voltage measurement circuit 65 measures the value of the voltage Vm(0) of the power source terminal 70. Thereafter, the constant current circuit 72 stops the output of the current, and the capacitor 91 is reset.

After the capacitor 91 is reset, the constant current circuit 72 outputs a constant current having a second value Ic(1) different from the first value Ic(0) to the power source line 30. Due to this, the charge of the capacitor 91 is started again. When the second period T12 has passed from a timing at which the charge of the capacitor 91 is started, the voltage measurement circuit 65 measures the value of the voltage Vm(1) of the power source terminal 70.

In the modified example of the second embodiment, a relationship shown in the following Expression (8) needs to be established.

$$I_c(0) \times T11 = I_c(1) \times T12 \tag{8}$$

The following Expression (9) is obtained from Expression (5) and Expression (6) described above.

$$V_m(0) - V_m(1) = \left( \frac{I_c(0) \times T11}{C_b} + R_c \times I_c(0) \right) - \left( \frac{I_c(1) \times T12}{C_b} + R_c \times I_c(1) \right) \tag{9}$$

The following Expression (10) is obtained from Expression (9) by using the relationship shown in Expression (8). The resistance calculation circuit 66 calculates the resistance value Rc in accordance with Expression (10).

$$R_c = \frac{V_m(0) - V_m(1)}{I_c(0) - I_c(1)} \tag{10}$$

The number of times multiplication is performed in Expression (10) is smaller than that of times multiplication is performed in Expression (7). Therefore, the amount of calculation in the resistance calculation circuit 66 is reduced, and a rounding error is reduced.

While preferred embodiments of the invention have been described and shown above, it should be understood that these are examples of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. An imaging device comprising a camera unit and a control unit connected to each other by a power source line, a first power source voltage transferred by the power source line being input to the camera unit as a second power source voltage, the camera unit including:
    an image sensor configured to generate a video signal by using the second power source voltage; and
    a capacitor configured to hold the second power source voltage; and
the control unit including:
    a voltage generation circuit configured to output the generated first power source voltage to the power source line;
    a voltage measurement circuit configured to measure a value of a voltage generated at a point connecting the power source line and the control unit,
        wherein the voltage at the point is generated based on both the second power source voltage held in the capacitor and a resistance component of the power source line;
    a resistance calculation circuit configured to calculate a resistance value of the power source line based on the value measured by the voltage measurement circuit; and a voltage adjustment circuit configured to adjust a value of the first power source voltage by controlling the voltage generation circuit based on the resistance value calculated by the resistance calculation circuit.

2. The imaging device according to claim 1,
wherein the control unit further includes a resistor electrically connected to the power source line,
wherein a value of a current flowing through the resistor in a first period is smaller than a value of a current flowing through the resistor in a second period different from the first period, and
wherein the resistance calculation circuit is configured to calculate the resistance value of the power source line based on a value of the second power source voltage in the first period, the value measured by the voltage measurement circuit in the second period, and a resistance value of the resistor.

3. The imaging device according to claim 2,
wherein the voltage measurement circuit is configured to measure the value of the voltage generated at the point in the first period based on the second power source voltage held in the capacitor, and
wherein the resistance calculation circuit is configured to use the value measured by the voltage measurement circuit in the first period as the value of the second power source voltage in the first period.

4. The imaging device according to claim 2,
wherein the first period and the second period are included in a blanking period of the image sensor.

5. The imaging device according to claim 3,
wherein the first period and the second period are included in a blanking period of the image sensor.

6. The imaging device according to claim 2,
wherein the control unit further includes a transistor configured to enter a high-impedance state or a low-impedance state,
wherein the resistor includes:
    a first terminal electrically connected to the power source line; and
    a second terminal electrically connected to the transistor,
wherein a state of the transistor is the high-impedance state in the first period, and
wherein the state of the transistor is the low-impedance state in the second period.

7. The imaging device according to claim 1,
wherein the camera unit and the control unit are connected to each other by a video signal line that transfers the video signal,
wherein the voltage adjustment circuit is configured to calculate a value of the second power source voltage in a video output period during which the video signal is output to the video signal line based on both the resistance value calculated by the resistance calculation circuit and a value of a current flowing through the power source line in the video output period, and
wherein the voltage adjustment circuit is configured to adjust the value of the first power source voltage such that the calculated value of the second power source voltage matches a target value.

8. The imaging device according to claim 1,
wherein the control unit further includes a constant current circuit configured to provide the power source line with a constant current used for charging the capacitor,
wherein the voltage measurement circuit is configured to measure a first value of the voltage at the point generated at a first timing of a current output period during which the constant current is output to the power source line, wherein the voltage measurement circuit is configured to measure a second value of the voltage generated at the point at a second timing of the current output period, wherein the second timing is different from the first timing, and wherein the resistance calculation circuit is configured to calculate the resistance value based on the first value and the second value.

9. An endoscope system, comprising a scope to be inserted into a living body; and the imaging device according to claim 1, wherein the camera unit is disposed in a distal end of the scope.

10. A control unit connected to a camera unit by a power source line, a first power source voltage transferred by the power source line being input to the camera unit as a second power source voltage used for driving an image sensor of the camera unit, the control unit comprising:

a voltage generation circuit configured to output the generated first power source voltage to the power source line;

a voltage measurement circuit configured to measure a value of a voltage generated at a point connecting the power source line and the control unit, wherein the voltage at the point is generated based on both the second power source voltage held in a capacitor of the camera unit and a resistance component of the power source line;

a resistance calculation circuit configured to calculate a resistance value of the power source line based on the value measured by the voltage measurement circuit; and a voltage adjustment circuit configured to adjust a value of the first power source voltage by controlling the voltage generation circuit based on the resistance value calculated by the resistance calculation circuit.

11. An imaging method in an imaging device including a camera unit and a control unit connected to each other by a power source line that transfers a first power source voltage, the first power source voltage transferred from the control unit by the power source line being input to the camera unit as a second power source voltage used for driving an image sensor of the camera unit, the method comprising:

a voltage output step in which a voltage generation circuit of the control unit generates the first power source voltage and outputs the generated first power source voltage to the power source line;

a voltage measurement step in which a voltage measurement circuit of the control unit measures a value of a voltage generated at a point connecting the power source line and the control unit, wherein the voltage at the point is generated based on both the second power source voltage held in a capacitor of the camera unit and a resistance component of the power source line;

a resistance calculation step in which a resistance calculation circuit of the control unit calculates a resistance value of the power source line based on the value measured by the voltage measurement circuit; and a voltage adjustment step in which a voltage adjustment circuit of the control unit adjusts a value of the first power source voltage by controlling the voltage generation circuit based on the resistance value calculated by the resistance calculation circuit.

* * * * *